United States Patent [19]

May et al.

[11] Patent Number: 4,650,808

[45] Date of Patent: Mar. 17, 1987

[54] SYNERGISTIC COMPOSITIONS CONTAINING HYDROXYPROPYL METHANETHIOLSULFONATE AND METHODS OF USING SAME

[75] Inventors: Oscar W. May, Memphis; Betty S. Johnson, Bartlett, both of Tenn.

[73] Assignee: Buckman Laboratories, Inc., Memphis, Tenn.

[21] Appl. No.: 594,056

[22] Filed: Mar. 28, 1984

[51] Int. Cl.$^4$ ............................................. A01N 43/80
[52] U.S. Cl. .......................................... 514/372; 71/67
[58] Field of Search ............................. 71/67; 514/372

[56] References Cited

U.S. PATENT DOCUMENTS 3,859,322  1/1975  Buckman et al. .................... 560/307
3,929,561 12/1975  Shema et al. ........................ 162/161
4,295,932 10/1981  Pocius ................................. 162/161
4,379,137  4/1983  Ehlers et al. ........................ 424/78

Primary Examiner—Catherine L. Mills
Attorney, Agent, or Firm—Finnegan, Henderson, Farabow, Garrett & Dunner

[57] ABSTRACT

Compositions comprising 2-hydroxypropyl methanethiolsulfonate in combination with a mixture of 5-chloro-2-methyl-4-isothiazolin-3-one and 2-methyl-4-isothiazolin-3-one show synergistic results in controlling the growth and proliferation of microorganisms in aqueous systems.

13 Claims, No Drawings

SYNERGISTIC COMPOSITIONS CONTAINING HYDROXYPROPYL METHANETHIOLSULFONATE AND METHODS OF USING SAME

BACKGROUND OF THE INVENTION

1. Field of the Invention

This invention relates to microbicidal compositions that are particularly suited to controlling the growth of microorganisms in aqueous systems. More particularly, compositions comprising combinations of a mixture of 5-chloro-2-methyl-4-isothiazolin-3-one and 2-methyl-4-isothiazolin-3-one with 2-hydroxypropyl methanethiolsulfonate are useful in controlling the growth and proliferation of slime-forming bacteria, fungi, and algae in commercial and industrial cooling water systems, cooling towers, evaporative condensers, air-washing systems, and industrial water supply and process water systems.

2. Description of the Prior Art

The formation of slime caused by the growth and multiplication of slime-forming microorganisms if not controlled is a serious problem. For example, lagoons, lakes, ponds, pools, and such systems as cooling water systems and pulp and paper mill systems all possess conditions which are conducive to the growth and reproduction of slime-forming microorganisms. In both once-through and recirculating cooling systems, for example, which employ large quantities of water as a cooling medium, the formation of slime by microorganisms is an extensive and constant problem.

Airborne organisms are readily entrained in the water from cooling towers and find this warm medium an ideal environment for growth and multiplication. Aerobic and heliotropic organisms flourish on the tower proper while other organisms colonize and grow in such areas as the tower sump and the piping and passages of the cooling system. Such slime serves to deteriorate the tower structure in the case of wooden towers. In addition, the deposition of slime on metal surfaces promotes corrosion. Furthermore, slime carried through the cooling system plugs and fouls lines, valves, strainers, etc. and deposits on heat exchange surfaces. In the latter case, the impedance of heat transfer can greatly reduce the efficiency of the cooling system.

In pulp and paper mill systems, slime formed by microorganisms is also frequently and, in fact, commonly encountered. Fouling or plugging by slime also occurs in the case of pulp and paper mill systems. Of greater significance, the slime becomes entrained in the paper produced to cause breaks on the paper machines with consequent work stoppages and the loss of production time or unsightly blemishes in the final product which result in rejects and wasted output. Likewise, lagoons, ponds, lakes and even pools, either used for pleasure purposes or used for industrial purposes for the disposal and storage of industrial wastes, become, during warm weather, excellent habitats for the growth reproduction of slime-forming microorganisms. In the case of the recreation areas, the problems of infection, etc., are obvious. In the case of industrial storage or disposal of industrial materials, the microorganisms cause additional problems which must be eliminated prior to either the materials' use or the disposal of the same in any type of waste disposal unit.

The previously discussed problems have resulted in the extensive utilization of biocides in cooling water and pulp and paper mill systems. Materials which have enjoyed wide-spread use in such applications include chlorine, organo-mercurials, chlorinated phenols, organo-bromines, and various organo-sulfur compounds. All of these compounds are generally useful for these purposes, but each is attended by a variety of impediments. For example, chlorine must be used at a high concentration for the effective control of organisms. This is probably true in part at least because chlorine is very reactive chemically thus reacting with various components present in the system before its full biocidal function can be achieved thus increasing cost. Other biocides are attended by odor problems and hazards in respect to storage, use or handling which limit their utility. To date, no one compound or type of compound has achieved a clearly established predominance in respect to the applications discussed.

Naturally, economy is a major consideration in respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides have exhibited a prolonged biocidal effect. Instead, their effectiveness is rapidly reduced as the result of exposure to physical conditions such as temperature, association with ingredients contained in the system toward which they exhibit an affinity or substantivity, etc., with a resultant restriction or elimination of their biocidal effectiveness.

As a consequence, the use of such biocides involves their continuous or frequent addition to systems to be treated and their addition to a plurality of points or zones in the systems to be treated. Accordingly, the cost of the biocide and the labor cost of such means of applying it are considerable. In other instances, the difficulty of access to the zone in which slime formation is experienced precludes the effective use of a biocide. For example, in a particular system there may be no access to an area at which slime formation occurs and the biocide may only be applied at a point which is upstream in the flow system. However, the physical or chemical conditions, e.g., chemical reactivity, thermal degradation, etc., which exist between the point at which the biocide may be added to the system and the point at which its biocidal effect is desired, may render the effective use of a biocide impossible.

Similarly, in a system experiencing relatively slow flow, such as a paper mill, if a biocide is added at the beginning of the system, its biocidal effect may be completely dissipated before it has reached all of the points at which this effect is desired or required. As a consequence, the biocide must be added at a plurality of points, and even then a graduated biocidal effect will be experienced between one point of addition to the system and the next point downstream at which the biocides may be added. In addition to the increased cost of utilizing and maintaining plural feed points, gross ineconomies in respect to the cost of the biocide are experienced. Specifically, at each point of addition, an excess of the biocide is added to the system in order to compensate for that portion of the biocide which will be expended in reacting with other constituents present in the system or experience physical changes which impair its biocidal activity.

It is disclosed in U.S. Pat. No. 3,859,322 that hydroxyalkyl esters of thiosulfonic acids are useful for the control of slime-forming microorganisms in industrial processes involving water. One such ester, 2-hydroxypropyl methanethiosulfonate, is now an article of commerce, being sold by Buckman Laboratories, Inc., under the tradename HPMTS.

It is disclosed in U.S. Pat. No. 3,929,561 that the mixture of 75% of 5-chloro-2-methyl-4-isothiazolin-3-one and 25% of 2-methyl-4-isothiazolin-3-one which is sold under the trademark Kathon ® 886 by Rohm and Haas may be blended with certain sulfones to produce a synergistic biocide. In U.S. Pat. No. 4,295,932, it is disclosed that combining the use of Kathon ® 886 along with treatment of an aqueous system with chlorine dioxide provides synergistic microbicidal action. In U.S. Pat. No. 4,379,137, it is disclosed that an admixture of a polymeric quaternary ammonium compound and compounds of the type of which Kathon ® 886 is composed is a synergistic disinfecting and preserving composition that is useful for protecting aqueous systems against contamination by deleterious microorganisms. Kathon ® 886 and these synergistic blends are claimed to be effective at low dosages, e.g., a few parts per million, for treating industrial water systems to control the growth of bacteria, fungi, and algae.

It is a principal object of our invention to provide a composition which obviates the disadvantages of the prior art biocidal compositions. Other objects and advantages of our invention will become apparent as the description proceeds.

SUMMARY OF THE INVENTION

In brief, we have discovered that by combining 2-hydroxypropyl methanethiosulfonate with a mixture of 5-chloro-2-methyl-4-isothiazolin-3-one and 2-methyl-4-isothiazolin-3-one a microbicidal composition is obtained that not only controls the growth of slime-forming microorganisms in industrial water systems but which also provides synergistic antimicrobial activity, i.e., the activity of the mixture is greater than the combined individual activities of the components of the mixture.

We have found that when the compositions of this invention are used to control the growth of microorganisms, synergistic results are noted when the amount of 5-chloro-2-methyl-4-isothiazolin-3-one in the isothiazoline mixture is greater on a weight basis than that of the 2-methyl-4-isothiazolin-3-one. Greater synergistic results are obtained when the weight ratios of the two compounds are used in the relative amounts of about 70% of the former and 30% of the latter compound. We generally prefer for the most effective synergistic results to use the compounds in the approximate ratio of 75% of the first compound and 25% of the second compound.

Thus, in a composition aspect of the invention, there is provided a microbicidal composition which comprises in admixture (a) the compound 2-hydroxypropyl methanethiolsulfonate; and (b) a mixture of 5-chloro-2-methyl-4-isothiazolin-3-one and 2-methyl-4-isothiazolin-3-one, wherein the weight ratio of the former is greater than the latter;

wherein the weight ratio of the thiolsulfonate to the isothiazoline mixture ranges from about 99:1 to about 1:99, respectively.

In a method aspect of the invention there is provided a method of inhibiting the growth and proliferation of microorganisms in an aqueous system which comprises treating the aqueous system with a biocidal amount of the above-defined microbicidal composition.

DESCRIPTION OF SPECIFIC EMBODIMENTS

The components comprising the composition of this invention are commercially available or easily synthesized from commercially available raw materials. The preparation of 2-hydroxypropyl methanethiolsulfonate is described in U.S. Pat. No. 3,859,322. A mixture of 75% 5-chloro-2-methyl-4-isothiazolin-3-one and 25% 2-methyl-4-isothiazolin-3-one is a commercially available product.

The ratios of the 2-hydroxypropyl methanethiolsulfonate to the mixtures of 5-chloro-2-methyl-4-isothiazolin-3-one and 2-methyl-4-isothiazolin-3-one in the composition of the invention are adjusted to provide a synergistic behavior to the composition. These synergistic ratios range from about 99:1 to 1:99, respectively, with the preferred ratios ranging from about 99:1 to 50:50, respectively.

The composition of the invention can be formulated as solutions in water. While the weight percent of the instant composition in the formulated solution can vary over a wide range, the solutions can conveniently be formulated to contain from about 5 to 25 percent by weight of the composition based on the total weight of the composition and the water. In formulating the solutions, other solvents which are water-miscible, such as ethyl alcohol, propyl alcohol, isopropyl alcohol, diethylene glycol, polyethylene glycol, diethylene glycol ethyl ether, and the like, may be employed in order to aid in solubilizing the active components. Furthermore, various other conventional additives may be employed, such as surfactants, dispersing agents, corrosion inhibitors, etc.

In utilizing the composition of the invention, a biocidally effective amount of the combination of the thiolsulfonate and the isothiazoline mixture should be added to the aqueous system. Although the amount to be employed will vary depending on the type of aqueous system to be treated as well as on other factors such as the degree of microbial contamination of the aqueous system, generally the composition of the invention is dissolved in the aqueous system in amounts of about 0.01 to 1000 parts of the composition to 1,000,000 parts of water. It will be understood, of course, that larger quantities of the composition may be used with no detrimental effect, but such larger quantities increase the cost of treatment with limited added material benefit.

In order to disclose the nature of the invention still more clearly, the following illustrative examples will be given. It is understood, however, that the invention is not to be limited to the specific conditions of details set forth in these examples, except insofar as such limitations are specified in the appended claims.

EXAMPLE 1

Synergism was demonstrated by testing 2-hydroxypropyl methanethiolsulfonate, designated as Compound A, and a mixture of 75% of 5-chloro-2-methyl-4-isothiazolin-3-one and 25% of 2-methyl-4-isothiazolin-3-one, designated as Compound B, in varying ratios over a range of concentrations and at three different pH values against the bacterium *Enterobacter aerogenes*. The compounds and mixtures were tested by the pulp-substrate method described in U.S. Pat. No. 2,881,070, which disclosure is hereby made a part of this application. The lowest concentration of each compound or mixture required for 80 percent kill of the bacterium was taken as the end point. End points for the mixtures of Compound A and Compound B were then compared with the end points for Compound A alone and Compound B alone. Synergism was determined by the method described by Kull, F. C., Eisman, P. C., Sylwestrowicz, H. D., and Mayer R. L., *Applied Microbiology* 9: 538–541 (1961) employing the ratio determined by $$\frac{Q_A}{Q_a} + \frac{Q_B}{Q_b}$$

wherein $Q_a$ = Concentration of Compound A in parts per million, acting alone, which produced an end point $Q_b$ = Concentration of Compound B, in parts per million, acting alone, which produced an end point $Q_A$ = Concentration of Compound A, in parts per million, in the mixture, which produced an end point $Q_B$ = Concentration of Compound B, in parts per million, in the mixture, which produced an end point When the sum of $Q_A/Q_a$ and $Q_B/Q_b$ is greater than one, antagonism is indicated and when the sum is equal to one, additivity is indicated. When less than one, synergism is demonstrated.

The procedure for demonstrating the synergism of the compositions of this invention is a widely used and accepted procedure. More detailed information is provided in the article by Kull et al. Further information concerning this procedure is contained in U.S. Pat. No. 3,231,509, which disclosure is hereby made a part of this application.

The results obtained in this example are shown in Table 1.

TABLE 1

| Weight Ratio of A to B | Test Organism: *Enterobacter aerogenes* | | | | | | | |
|---|---|---|---|---|---|---|---|---|
| | Quantities Producing End Points (ppm) | | | | | $\frac{Q_A}{Q_a}$ | $\frac{Q_B}{Q_b}$ | $\frac{Q_A}{Q_a} + \frac{Q_B}{Q_b}$ |
| | $Q_a$ | $Q_A$ | $Q_b$ | $Q_B$ | Mixt. | | | |
| pH: 5.5 | | | | | | | | |
| 100/0 | 0.04 | — | — | — | — | — | — | — |
| 87/13 | — | 0.035 | — | 0.005 | 0.04 | 0.88 | 0.08 | 0.96 |
| 0/100 | — | — | 0.06 | — | — | — | — | — |
| pH: 6.5 | | | | | | | | |
| 100/0 | 0.08 | — | — | — | — | — | — | — |
| 87/13 | — | 0.035 | — | 0.005 | 0.04 | 0.44 | 0.13 | 0.57 |
| 0/100 | — | — | 0.04 | — | — | — | — | — |
| pH: 7.5 | | | | | | | | |
| 100/0 | 0.40 | — | — | — | — | — | — | — |
| 87/13 | — | 0.070 | — | 0.010 | 0.08 | 0.18 | 0.25 | 0.43 |
| 0/100 | — | — | 0.04 | — | — | — | — | — |

Using the method described by Kull et al., the sums of $Q_A/Q_a + Q_B/Q_b$ for a mixture containing 87 parts of Compound A to 13 parts of Compound B were calculated. As shown in Table 1, these were 0.96, 0.57, and 0.43 at pH 5.5, 6.5, and 7.5, respectively. Since all of these sums are less than 1, synergism is demonstrated, with the greatest degree of synergism being indicated at the higher pH values.

EXAMPLE 2

The effectiveness of Compounds A and B described in Example 1, and of a mixture of A and B, was determined against *Pseudomonas aeruginosa* at pH 6.5, using the same pulp substrate method referred to in Example 1. The method of Kull et al. described in Example 1 was then used to demonstrate that a synergistic effect was also obtained in controlling the test bacterium. The end point in these calculations was again the concentration in parts per million required for 80 percent kill. The results of these tests are shown in Table 2.

TABLE 2

| Weight Ratio of A to B | Test Organism: *Pseudomonas aeruginosa* pH: 6.5 | | | | | | | |
|---|---|---|---|---|---|---|---|---|
| | Quantities Producing End Points (ppm) | | | | | $\frac{Q_A}{Q_a}$ | $\frac{Q_B}{Q_b}$ | $\frac{Q_A}{Q_a} + \frac{Q_B}{Q_b}$ |
| | $Q_a$ | $Q_A$ | $Q_b$ | $Q_B$ | Mixt. | | | |
| 100/0 | 1.0 | — | — | — | — | — | — | — |
| 87/13 | — | 0.35 | — | 0.05 | 0.40 | 0.35 | 0.50 | 0.85 |
| 0/100 | — | — | 0.10 | — | — | — | — | — |

EXAMPLE 3

The effectiveness of Compound A and Compound B described in Example 1 and of a mixture of A and B was determined against the bacterium *Sphaerotilus natans* in Stokes broth, an aqueous solution with the following composition:

| Compound | Grams per liter |
|---|---|
| Peptone | 1.0 |
| Glucose | 1.0 |
| Magnesium sulfate heptahydrate | 0.2 |
| Calcium chloride | 0.05 |
| Ferric chloride hexahydrate | 0.01 |

The broth was adjusted to pH 7.0 with sodium hydroxide. Forty-gram portions were added to 180-milliliter Pyrex milk dilution bottles fitted with Escher rubber stoppers and then sterilized. Each of the following substances were then added to the bottles in the order listed:

1. Sterile distilled water as required in each individual case to bring the total weight of the contents of each bottle to 50 grams after all subsequent additions specified hereinafter (including inoculation with the aqueous suspension of test organism) have been made;
2. Solution of toxicant or control agent to be evaluated in such individual volumes as to give the concentration desired in parts per million by weight;
3. Five milliliters of sterile solution of pH 6.5 buffer;
4. One milliliter of a 24-hour old *Sphaerotilus natans* culture grown in Stokes broth.

After the inoculant suspension of the test organism was added to the bottles they were allowed to stand for 18 hours at an incubation temperature of 28 degrees Celsius, at which time a portion of the broth was withdrawn, diluted, plated on Stokes agar, and incubated for 72 hours at 28 to 30 degrees Celsius. Stokes agar was prepared like the broth with 12.5 grams of agar added per liter. The number of colonies on each agar plate was determined, and the results were converted to the count per milliliter of substrate.

From these data, the percentage kills were calculated. The difference between the count for the control substrate (with no toxicant) and the count obtained from the substrate containing toxicant was divided by the count for the control substrate to get the fraction killed, which was then converted to percent killed by multiplying by 100.

The data from these tests were used to determine synergism by the method of Kull et al. described in Example 1. The results are shown in Table 3.

TABLE 3

Test Organism: *Sphaerotilus natans*
pH: 6.5

| Weight Ratio of A to B | Quantities Producing End Points (ppm) | | | | | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|---|---|
| | $Q_a$ | $Q_A$ | $Q_b$ | $Q_B$ | Mixt. | | | |
| 100/0 | 1.5 | — | — | — | — | — | — | — |
| 87/13 | — | 0.35 | — | 0.05 | 0.40 | 0.23 | 0.50 | 0.73 |
| 0/100 | — | — | 0.10 | — | — | — | — | — |

EXAMPLE 4

In order to show the synergism of mixtures of Compound A and Compound B with different ratios of A to B, tests were run with mixtures having ratios of 95 parts of A to 5 parts of B, 50 parts of A to 50 parts of B, and 5 parts of A to 95 parts of B, respectively. The tests were run against the bacterium *Enterobacter aerogenes* as described in Example 1. The results are shown in Table 4, and they demonstrate the synergism of all the mixtures.

TABLE 4

Test Organism: *Enterobacter aerogenes*

| Weight Ratio of A to B | Quantities Producing End Points (ppm) | | | | | $\frac{Q_A}{Q_a}$ | $\frac{Q_B}{Q_b}$ | $\frac{Q_A}{Q_a} + \frac{Q_B}{Q_b}$ |
|---|---|---|---|---|---|---|---|---|
| | $Q_a$ | $Q_A$ | $Q_b$ | $Q_B$ | Mixt. | | | |
| pH: 5.5 | | | | | | | | |
| 100/0 | 0.04 | — | — | — | — | — | — | — |
| 95/5 | — | 0.038 | — | 0.002 | 0.04 | 0.95 | 0.03 | 0.98 |
| 50/50 | — | 0.0175 | — | 0.0175 | 0.035 | 0.44 | 0.29 | 0.73 |
| 5/95 | — | 0.0025 | — | 0.0475 | 0.05 | 0.06 | 0.79 | 0.85 |
| 0/100 | — | — | 0.06 | — | — | — | — | — |
| pH: 6.5 | | | | | | | | |
| 100/0 | 0.08 | — | — | — | — | — | — | — |
| 95/5 | — | 0.0475 | — | 0.0025 | 0.05 | 0.59 | 0.06 | 0.65 |
| 50/50 | — | 0.02 | — | 0.02 | 0.04 | 0.25 | 0.50 | 0.75 |
| 5/95 | — | 0.0015 | — | 0.0285 | 0.03 | 0.02 | 0.71 | 0.73 |
| 0/100 | — | — | 0.04 | — | — | — | — | — |
| pH: 7.5 | | | | | | | | |
| 100/0 | 0.40 | — | — | — | — | — | — | — |
| 95/5 | — | 0.19 | — | 0.01 | 0.20 | 0.48 | 0.25 | 0.73 |
| 50/50 | — | 0.03 | — | 0.03 | 0.06 | 0.08 | 0.75 | 0.83 |
| 5/95 | — | 0.0018 | — | 0.0332 | 0.035 | 0.01 | 0.83 | 0.84 |
| 0/100 | — | — | 0.04 | — | — | — | — | — |

While particular embodiments of the invention have been described, it will be understood, of course, that the invention is not limited thereto since many modifications may be made, and it is, therefore contemplated to cover by the appended claims any such modifications as fall within the true spirit and scope of the invention.

The invention having thus been described, what is claimed and desired to be secured by Letters Patent is:

1. A synergistic bactericidal composition comprising in admixture
   (a) 2-hydroxypropyl methanethiosulfonate; and
   (b) a mixture of 5-chloro-2-methyl-4-isothiazolin-3-one and 2-methyl-4-isothiazolin-3-one, wherein the approximate weight ratio of the compounds in the mixture (b) is from about 70 to 80 parts by weight 5-chloro-2-methyl-4-isothiazolin-3-one to about 20 to 30 parts by weight 2-methyl-4-isothiozolin-3-one; and characterized further in that the weight ratio of the thiosulfonate (a) to the isothiazoline mixture (b) ranges from about 95:5 to about 5:95.

2. The composition of claim 1 where said ratio of (a) to (b) is about 87:13.

3. The composition of claim 1 where said ratio of (a) to (b) is about 90:10.

4. The composition of claim 1 where said ratio of (a) to (b) is about 50:50.

5. The composition of claim 1 wherein the approximate weight ratio of the compounds in the mixture (b) is 70 parts of 5-chloro-2-methyl-4-isothiazolin-3-one to 30 parts of 2-methyl-4-isothiazolin-3-one.

6. The composition of claim 1 wherein the approximate weight ratio of the compounds in the mixture (b) is 75 parts of 5-chloro-2-methyl-4-isothiazolin-3-one to 25 parts of 2-methyl-4-isothiazolin-3-one.

7. The composition of claim 1 wherein the approximate weight ratio of the compounds in the mixture (b) is 80 parts of 5-chloro-2-methyl-4-isothiazolin-3-one to 20 parts of 2-methyl-4-isothiazolin-3-one.

8. A method of controlling the growth of bacteria in aqueous systems which comprises adding to the water in such system a composition as defined in claim 1 in an amount between approximately 0.01 and approximately 1000 parts of the composition per million parts of water.

9. The method of claim 8 in which the aqueous system is that of a pulp and paper mill system.

10. The method of claim 8 in which the aqueous system is that of a cooling water system.

11. The method of claim 8 in which the aqueous system is that of a petroleum enhanced oil recovery waterflood system.

12. The synergistic bactericidal composition of claim 2, wherein said composition is synergistic against at least one bacterium selected from the group consisting of *Enterobacter aerogenes, Psuedomonas aeruginosa* and *Sphaerotilus natans*.

13. The synergistic bactericidal composition of claim 12, wherein said composition is synergistic against *Enterobacter aerogenes*.

* * * * *